United States Patent [19]

Pugach

[11] 4,169,809

[45] Oct. 2, 1979

[54] EXTRACTIVE PURIFICATION OF CARBOXYLIC ACIDS CONTAINING MONOVALENT AND TRIVALENT THALLIUM CARBOXYLATES

[75] Inventor: Joseph Pugach, Ho-Ho-Kus, N.J.

[73] Assignee: Halcon Research & Development Corporation, New York, N.Y.

[21] Appl. No.: 896,401

[22] Filed: Apr. 14, 1978

[51] Int. Cl.$^2$ .......................... C01F 15/00; C07F 5/00
[52] U.S. Cl. .................................. 252/186; 423/111; 423/495
[58] Field of Search .................... 252/186; 260/429 R; 423/111, 395, 495, 544, 659

[56] References Cited

U.S. PATENT DOCUMENTS

| | | | |
|---|---|---|---|
| 4,113,756 | 11/1976 | Johnson | 260/429 R |
| 4,115,420 | 4/1977 | Brill | 260/429 R |

*Primary Examiner*—Benjamin R. Padgett
*Assistant Examiner*—Irwin Gluck
*Attorney, Agent, or Firm*—William C. Long; David Dick; Jack B. Murray, Jr.

[57] ABSTRACT

A process is provided for extracting monovalent thallium and alkali metal values from a liquid medium containing a carboxylic acid having limited solubility in water and containing dissolved trivalent thallium values, monovalent thallium values and, optionally, alkali metal compound, which comprises contacting the carboxylic acid medium with an extractant comprising an acidic aqueous medium having a pH of not greater than about 6 to preferentially extract monovalent thallium and alkali metal values into the aqueous medium, and recovering a raffinate comprising a treated carboxylic acid medium containing trivalent thallium carboxylate and depleted of monovalent thallium and alkali metal values.

8 Claims, No Drawings

EXTRACTIVE PURIFICATION OF CARBOXYLIC ACIDS CONTAINING MONOVALENT AND TRIVALENT THALLIUM CARBOXYLATES

BACKGROUND OF THE INVENTION

1. Field of the Invention

This invention relates generally to the purificaion of impure solutions of trivalent thallium compounds, and more specifically to the treatment of carboxylic acid media containing dissolved trivalent thallium carboxylates and monovalent thallium carboxylates.

2. Description of the Prior Art

Trivalent thallium compounds, i.e., thallic compounds, have been used as oxidizing agents in various reactions. For example, Kruse et al. J. Org. Chem. 36, 1154 (1971) describes the epoxidation of certain olefins with thallic acetate, and U.S. Pat. No. 3,641,067 (issued in 1972 to W. Kruse) relates to the preparation of the epoxides of propylene and isobutylene by means of lower thallic alkanoates.

In all of these reactions the trivalent thallium is reduced to the monovalent state and if the thallium is to be reused in the reaction it is necessary to reoxidize or "regenerate" it by converting thallium (I) to thallium (III). Various methods for effecting this conversion have been proposed. Thus, it is proposed to convert thallium (I) to thallium (III) in the application of William Brill, entitled "Catalytic Conversion of Thallium (I) to Thallium (III)", Ser. No. 789,053, filed Apr. 21, 1977 now U.S. Pat. No. 4,115,420 by means of molecular oxygen using a Group VIII noble metal as a catalyst. In addition, it has been proposed in the application of Richard A. Johnson entitled, "Conversion of Monovalent Thallium to Tri-valent Thallium," Ser. No. 740,147, filed Nov. 8, 1976 now U.S. Pat. No. 4,113,756 to convert thallium (I) to thallium (III) by means of molecular oxygen in the presence of a Group VIII noble metal catalyst and in the presence of a promoter comprising an alkali metal compound. The processes of both Ser. No. 789,053 and Ser. No. 740,147 typically result in an aqueous solution containing the desired trivalent thallium compound together with unconverted monovalent thallium compound and alkali metal compound, where the latter is employed as promoter in accordance with Ser. No. 740,147. It is generally desirable to recover the trivalent thallium compound so produced to avoid passing monovalent thallium compound and alkali metal compound (where present) as impurities to the subsequent reaction steps using the trivalent thallium compound.

In an application of Richard A. Johnson, entitled "Extractive Recovery of Trivalent Thallium Values from Aqueous Solutions," Ser. No. 896,550 said application being filed on even date herewith (and which is hereby incorporated by reference), a method of removing trivalent thallium values from aqueous solutions containing trivalent thallium values, monovalent thallium values, and optionally, alkali metal compound, is disclosed in which the aqueous solution is contacted with an extractant comprising a carboxylic acid having limited solubility with water to preferentially extract at least a portion of the dissolved trivalent thallium values into the carboxylic acid. A carboxylic acid extract containing the extracted trivalent thallium values is then recovered as a separate phase. While such a process efficiently removes trivalent thallium values from aqueous solutions of the same, monovalent thallium and alkali metal values (where present) can also be extracted to some extent by the carboxylic acid extractant. Removal of residual monovalent thallium and alkali metal values from the carboxylic acid extract is therefore desirable to further isolate the trivalent thallium values. Treatment of the carboxylic acid extract for precipitation of monovalent thallium as the halide and use of ion-exchange resins to remove alkali metal values as suggested in the above application of R. Johnson are effective, but an alternative method would be desirable. While the water back-extraction suggested in the above application of R. Johnson results in the removal of a portion of the undesired monovalent thallium and alkali metal values, a need exists for a more efficient extraction process.

In Japanese Patent Application application 50-92296 (published July 23, 1975), trivalent thallium ions are extracted from aqueous solutions containing the same by using a polar organic solvent in the presence of bromine and/or chlorine ions and hydrogen bromide and/or hydrogen chloride to form an extractant containing the corresponding halogen thallium acid (e.g., $HTlBr_4$, $HTlCl_4$, etc.), and the extractant so produced is simultaneously contacted with a small amount of water and a water-immiscible non-polar organic solvent, whereby the trivalent thallium ions are reextracted into the aqueous phase as the halogen thallium acid. This process is disadvantageous for treatment of aqueous solutions containing both monovalent and trivalent thallium values in that any monovalent thallium ions will be precipitated as the corresponding halide, which precipitate must then be recovered and treated for conversion of the monovalent thallium content thereof to a water-soluble form before further processing can be effected, e.g., before recycle of the monovalent thallium values to an oxidation step in which trivalent thallium values are formed therefrom.

Other extraction techniques have been developed as analytical tools for recovery of trivalent thallium ions from aqueous solutions, employing such extractants as diethyldithiocarbamate and 8-quinolinol-4-thenoyltrifluoroacetone, as outlined in G. H. Morrison and H. Freiser, "Solvent Extraction in Analytical Chemistry" 237 (John Wiley & Sons 1957). However, such analytical extraction methods are not readily adaptable to industrial processes and offer the disadvantage of the extreme high cost of such extractants on an industrial scale.

Likewise, recovery of trivalent thallium ions in the form of $TlCl_4^-$ using an anion exchange resin as suggested in U.S. Pat. No. 3,399,956 (issued in 1968 to I. Hirose et al.) is disadvantageous due to the high cost of the resin required for recovery of large amounts of trivalent thallium in an industrial scale process.

Other extraction methods employed for treatment of liquids containing monovalent thallium are not readily adaptable to separation of trivalent thallium from aqueous mixtures containing monovalent thallium. See U.S. Pat. No. 4,031,196 (issued in 1977 to J. J. Leonard)(extraction of isobutyric acid with dibutyl ether from aqueous medium also containing barium salt and thallous isobutyrate) and A. Letheridge et al., J. Chem. Soc. Perkins I, p. 2763 (1973) (extraction of aqueous mixture containing thallous trifluoroacetate and octene-1 oxidation products with ether). However, the aqueous media treated in these references, did not contain trivalent thallium.

SUMMARY OF THE INVENTION

It has been surprisingly found that monovalent thallium and alkali metal values can be rapidly and efficiently extracted from a liquid (hereinafter also referred to as the "carboxylic acid medium") containing a carboxylic acid having limited solubility containing monovalent thallium and alkali metal values together with dissolved trivalent thallium values by a process which comprises contacting the liquid with an extractant comprising an acidic aqueous medium having a pH of not greater than about 6 to preferentially extract monovalent thallium and alkali metal values into the aqueous medium and recovering a carboxylic acid raffinate containing trivalent thallium values and depleted of monovalent thallium and alkali metal values.

By this process, it has been found possible to remove substantial amounts of monovalent thallium and alkali metal values from the carboxylic acid medium, and to obtain a carboxylic acid raffinate containing trivalent thallium values which is depleted of monovalent thallium and alkali metal values. Moreover, it has been surprisingly found that substantially all of the trivalent thallium values remain in the carboxylic acid phase and only very minor amounts, if any, are extracted by the acidic aqueous medium, thereby providing an efficient extractive purification of the treated carboxylic acid medium.

The facile separation of thallic values from thallous values and alkali metal values is also surprising in view of the double salts known to be found between thallium (III) and thallium (I) compounds and between such thallium compounds and alkali metals cations. See, e.g., A. South, Jr. et al., *JACS*, vol. 90, no. 25, 7064 (1968) and R. J. Oullette et al., *J. Org. Chem.*, vol. 35, no. 10, 3210 (1970), as to thallium (III)—thallium (I) double salts and F. Challenger et al., *J. Chem. Soc.* 405 (1934); J. H. Pratt, *J. Amer. Chem. Soc.* vol. 49, p. 404, (1895); and G. Newman, *Ann.*, vol. 244, p. 329 (1888), as to mixed thallium—alkali metal salts.

DETAILED DESCRIPTION OF THE INVENTION

In accordance with the process of the present invention, a carboxylic acid medium containing dissolved therein trivalent thallium values, monovalent thallium values, and, optionally, at least one alkali metal compound, is contacted with an extractant comprising an acidic aqueous medium having a pH of not greater than about 6, to preferentially extract from the carboxylic acid medium at least a portion of the dissolved monovalent thallium and alkali metal values into the acidic aqueous medium, preferably in the substantial absence of free halide, to avoid precipitation of monovalent thallium halide. As used herein, monovalent thallium and alkali metal values are termed to be "preferentially extracted" when the proportion of the monovalent thallium and alkali metal values originally present in the carboxylic acid medium which are extracted into the acidic aqueous extractant by the process of the present invention is greater than the proportion of the trivalent thallium values originally present in the carboxylic acid medium which are extracted into the extractant. Thus, while some trivalent thallium values can also pass into the acidic aqueous extractant, the equilibrium distribution coefficients for monovalent thallium cation and alkali metal cations in the carboxylic acid aqueous systems of the present invention have been surprisingly found to be much less than the equilibrium distribution coefficients for trivalent thallium, the equilibrium distribution coefficients being defined by the expression (I):

$$k_a = \frac{C_a}{C'_a} \quad \text{(I)}$$

wherein $k_a$ is the equilibrium distribution coefficient for component "a", $C_a$ is the concentration of component "a" in the carboxylic acid phase, and $C'_a$ is the concentration of component "a" in the aqueous phase.

For example, the equilibrium distribution ("$k_{Tl3}$") for trivalent thallium cations is given by the expression (II):

$$k_{Tl3} = \frac{c_{Tl3}}{c'_{Tl3}} \quad \text{(II)}$$

and the equilibrium distribution coefficient ("$k_{Tl1}$") for monovalent thallium cations is given by the expression (III):

$$k_{Tl1} = \frac{c_{Tl1}}{c'_{Tl1}} \quad \text{(III)}$$

Thus, for monovalent thallium to be "preferentially extracted" in accordance with the process of this invention, "$\alpha_1$" should be greater than 1, and preferably greater than 2, wherein "$\alpha_1$" is defined by the following expression (IV):

$$\alpha_1 = \frac{k_{Tl3}}{k_{Tl1}} \quad \text{(IV)}$$

and "$\alpha_2$" should be greater than 1, and preferably greater than 2, wherein "$\alpha_2$" is defined by the following expression (V):

$$\alpha_2 = \frac{k_{Tl3}}{k_{A.M.}} \quad \text{(V)}$$

wherein "$k_{A.M.}$" is the equilibrium distribution coefficient for alkali metal cation.

Carboxylic acid media treated by the process of the present invention comprise mono- and di-carboxylic acids, both substituted and unsubstituted, which have limited solubility in water, and which contain, dissolved therein, trivalent and monovalent thallium carboxylate and, optionally, alkali metal compound. The term "limited solubility in water" as used herein is intended to refer to carboxylic acids having a solubility in water at 20° C. of less than about 10 grams of acid per 100 grams of water. More preferably, however, the carboxylic acid possesses a solubility in water at 20° C. of less than about 2 grams of acid per 100 grams of water, and most preferably less than about 0.2 gram of acid per 100 grams of water.

Useful carboxylic acids which may be employed in the practice of this invention therefore include monocarboxylic acids of the formula (1):

wherein $R^1$, $R^2$ and $R^3$ are the same or different and are selected from the group consisting of hydrogen, alkyl, cycloalkyl, aryl, alkaryl, aralkyl, derivatives of the foregoing groups wherein one or more carbon-bonded hydrogen atom is replaced by alkyl, cycloalkyl, an aryl group or by a halide atom, and derivatives of the foregoing roups wherein one or more carbon atom is replaced by an oxygen atom, with the proviso that $R^3$ cannot be hydrogen when $R^1$ and $R^2$ are each hydrogen, and with the further proviso that the monocarboxylic acid contains at least 5 carbon atoms per molecule; and mixtures of the foregoing.

When $R^1$, $R^2$ and $R^3$ is alkyl, the alkyl group can be branched or straight chained and is generally from 1 to 20 carbon atoms, preferably from 1 to 8 carbon atoms. Exemplary of such alkyl groups are methyl, ethyl, propyl, isopropyl, butyl, isobutyl, pentyl, hexyl, heptyl, octyl, decyl, dodecyl, octadecyl and the like. When $R^1$, $R^2$ or $R^3$ is aryl, the aryl group is generally phenyl, tolyl, or naphthyl. When $R^1$, $R^2$ or $R^3$ is cycloalkyl, the cycloalkyl group is generally from 3 to 12 carbon atoms, and preferably from 5 to 8 carbon atoms. Exemplary of such cycloalkyl groups are cyclopropyl, cyclohexyl, cyclodecyl, cyclododecyl, dicyclohexyl, and the like. When $R^1$, $R^2$ or $R^3$ is alkaryl, the aryl component generally consists of phenyl or tolyl and the alkyl component generally has from 1 to 20 carbon atoms, and preferably from 1 to 8 carbon atoms. Examples of such aryl groups are 3-tolyl, 4-ethylphenyl, 3-xylyl, 4-isopropylphenyl, 2-butyl, 4-phenyl and the like. When $R^1$, $R^2$ or $R^3$ is aralkyl, the aryl group generally consists of phenyl or alkyl-substituted phenyl and the alkyl component generally has from 1 to 20 carbon atoms, and preferably from 1 to 8 carbon atoms. Examples of such aralkyl groups are benzyl, 2,2-diphenylmethyl, and the like. The alkyl, cycloalkyl and aryl substituents on the substituted derivatives of the foregoing are similarly defined. Halide atoms which can be substituted on the foregoing include chloro-, bromo-, iodo- and fluoro-atoms. Ether derivatives of the foregoing groups in which a non-carbonyl carbon atom is replaced by an oxygen atom are, for example, in the case of alkyl groups, exemplified by alkaoxy-substituted alkyl such as 2-methoxyhexyl and 3-ethoxypropyl, and, in the case of aralkyl groups exemplified by phenoxy-substituted alkyl such as phenoxymethyl, benzoxyethyl, 4-phenoxyhexyl and the like.

Exemplary of monocarboxylic acids which may be employed, therefore, are straight-chained acids such as hexanoic acid, heptanoic acid, octanoic acid, decanoic acid, undecanoic acid, dodecanoic acid, tridecanoic acid, heptadecanoic acid, myristic acid, palmitic acid, stearic acid, and the like; straight-chained dicarboxylic acids such as adipic acid, pimelic acid, suberic acid, azelaic acid, sebacic acid, and the like; branched-chain derivatives of the foregoing such as 2-ethylbutyric acid, 2,2-diethylbutyric acid, 2,2-dimethylpropanoicacid, 2,2-dimethylbutyric acid, 4-methylhexanoic acid, 2-methyldecanoic acid, 2-ethylhexanoic acid, 4-methylpentanoic acid, 4-ethylnonanoic acid, 2-ethyl-3-methylpropanoic acid, 2-ethyl-2-(n-propyl) pentanoic acid and the like; and substituted derivatives of the foregoing including cyclohexyl acetic acid, 2-chloro-2-methylbutyric acid, triphenyl acetic acid, 2-bromo-2-phenyl propionic acid, 2-ethyl-2-methyl butyric acid, 4-chlorobutyric acid, 4-phenoxy butyric acid and the like.

Examplary of dicarboxylic acids which are useful include straight-chained acids such as butanedioic acid, hexanedioic acid, heptanedioic acid, octanedioic acid, nonanedioic acid, decanedioic acid and the like, substituted derivatives of the foregoing including 2-methyl, 3-dodecyl butanedioic acid, phenyl butanedioic acid, tetramethyl butanedioic acid and the like. Preferred among the foregoing carboxylic acids are the monocarboxylic acids having at least 6 carbon atoms per molecule, and most preferred are such acids having from 6 to 12 carbon atoms per molecule. Exemplary of carboxylic acids which are preferred for use in the present invention are members selected from the group consisting of hexanoic acid, octanoic acid, pivalic acid and neodecanoic acid.

A wide variety of anions can be associated with the trivalent thallium values and monovalent thallium values present in the carboxylic acid medium which is treated in accordance with the invention. Typically, the anions will comprise carboxylate anions derived from alkyl carboxylic acids containing at least 6 carbon atoms, and preferably from 6 to 12 carbon atoms per acid molecule. Exemplary of such carboxylate anions are therefore, the hexanoate, 2-ethylhexanoate, octanoate, 2-ethyl-2-butyl-pentanoate, neodecanoate, undecanoate, pivalate, and the like, and mixtures thereof. The anion of the monovalent thallium values can be the same as, or different from, the anion of the trivalent thallium values contained in the carboxylic acid medium, and the carboxylate anion of the monovalent thallium in the acidic aqueous extract can differ from the anion of the monovalent thallium in the carboxylic acid medium which is treated. For example, when octanoic acid media containing thallic octanoate and thallous octanoate are extracted with an aqueous acetic acid solution in accordance with the process of this invention, the anion of the thallic and thallous values in the acidic aqueous extract which is recovered will be found to be predominantly the acetate. Thus, the terms "trivalent thallium values" and monovalent thallium values" are used herein for convenience to refer to the cations $Tl+^3$ and $Tl+^1$, respectively, which are dissolved in the liquid medium to which these terms are applied and are used without regard to the anions with which such cations are associated.

The alkali metal compound which can be optionally present in the carboxylic acid medium treated in accordance with the present invention can be derived from any of the alkali metal compounds employed as promoters as described in Ser. No. 740,147, referred to above, which is hereby incorporated herein by reference. Thus, the alkali metal compound can comprise compounds of sodium, potassium, rubidium, cesium and lithium. Typical compounds are the oxides, salts, both organic and inorganic such as the carboxylates and the like. The anion of the alkali metal compound most preferably corresponds to the anion associated with the monovalent thallium carboxylate to be extracted by the process of this invention. Of course, the precise form of the alkali metal values in the carboxylic acid medium will vary depending on the degree to which such alkali metal compound is converted to another form by other ingredients of the carboxylic acid medium. For example, when the carboxylic acid medium contains hexanoic acid, the alkali metal values of such a medium will generally be in the form of the corresponding alkali metal carboxylate (e.g., sodium hexanoate). However, this is not critical to the practice of the present invention and, for convenience, the term "alkali metal compound" is for convenience used herein to refer to alkali metal cations (e.g., $Na^{+1}$, $K^{+1}$, $Rb^{+1}$ and the like)

dissolved in the liquid medium to which this term is applied and is used without regard to the anion associated with such alkali metal cations. It will be understood that the anion associated with the alkali metal cations extracted into the acidic aqueous extractant can differ from the anion associated with such cations in the carboxylic acid medium treated by this invention. Thus, alkali metal octanoate contained in an octanoic acid medium will, by virtue of extraction with an acetic acid extractant in accordance with this invention, be present in the extract predominently in the form of the acetate.

The concentrations of monovalent thallium carboxylate, trivalent thallium carboxylate and alkali metal compound in the carboxylic acid medium treated by the process of the present invention is not in any way critical. Preferably, any solids, including solid mono- or tri-valent thallium carboxylate or solid alkali metal compound present in the carboxylic acid medium, are first removed by conventional techniques such as filtration, centrifuging or allowing the carboxylic acid medium containing the solids to settle and decanting the solution, in order to obtain a carboxylic acid medium substantially free of solids for treatment in accordance with the process of the present invention. However, this is not required, and a carboxylic acid medium containing such solids in addition to dissolved monovalent and trivalent thallium values and alkali metal compound may be also treated in accordance with the present invention.

Water-immiscible organic solvents can be employed in the carboxylic acid medium to facilitate the handling of the more viscous carboxylic acids when employed in the carboxylic acid medium to be extracted and are especially preferred when dicarboxylic acids are employed. Water-immiscible organic solvents which are suitable include aromatic hydrocarbons, such as benzene, toluene, and the like; aliphatic hydrocarbons, such as pentane, hexane, iso-octane, cyclohexane, and the like; petroleum ether; alkyl ethers, such as diisopropyl ether, dimethyl ether, and the like; monocarboxylic acid esters, such as amyl acetate, methyl octanoate, and the like; organic alcohols such as amyl alcohol, octanol, and the like; chlorohydrocarbons, such as chloroform, carbon tetrachloride, methylene chloride, and the like; substituted aromatic hydrocarbons, such as chlorobenzene, nitrobenzene, anisole, acetophenone, and the like; ketones and diketones, such as octanone, acetylacetone, and the like; and nitriles, such as butyronitrile, benzonitrile, and the like. The amount of such organic solvent in the carboxylic acid medium is not critical to the process of the present invention, but will generally be employed in an amount of from about 5 to 80 weight percent, and preferably from about 15 to 60 weight percent of the amount of the carboxylic acid in the medium.

While not critical to the practice of the process of this invention, the carboxylic acid and the aqueous medium extractant, as indicated above, are preferably substantially free of free halide ions to avoid precipitation of monovalent thallium halides.

The acidic aqueous extractant employed in the process of the present invention comprises an aqueous solution having a pH of not greater than about 6, and more preferably not greater than about 5.5, to avoid complicating the recovery of trivalent values from the resulting aqueous extract as a result of the precipitation of substantial amounts of thallic oxide in alkaline media. The acidifying agent present in the aqueous extractant is not critical and can comprise any acid which possesses a solubility in water of at least 0.5 gram per 100 grams of water, and preferably at least 20 grams per 100 grams of water, as determined at 25° C. Most preferably, the selected acidifying agent is substantially insoluble in the carboxylic acid media to be treated, although this is not critical. Generally the acidifying agent will comprise a member selected from the group consisting of organic acids, inorganic acids, phenol, sulfonic acids, and mixtures thereof. A wide variety of organic and inorganic acids can be used. Suitable inorganic acids include mineral acids, such as sulfuric acid, nitric acid, phosphoric acid, perchloric acid, and the like. Suitable organic acids include lower alkanoic acids such as formic acid, acetic acid, propionic acid, butyric acid, isobutyric acid, and halogenated derivatives thereof, such as mono-, di-, and tri-chloracetic acid, trifluoroacetic acid and the like. Suitable sulfonic acids include para-toluene sulfonic acid, methane sulfonic acid, and the like. The amount of the selected acidifying agent which is employed in the aqueous extractant will, of course, depend on the particular acidifying agent to be employed, and can be easily ascertained by the skilled practitioner. Generally, however, the acidifying agent will be employed in the aqueous extractant in a concentration of from about 0.1 to 5 moles per liter, and preferably from about 0.5 to 3 mole per liter. While not critical to the present invention, the acidifying agent is preferably intimately admixed with the aqueous component of the extractant prior to contact with the carboxylic acid media to be treated.

While also not critical to the process of the present invention, the acidic aqueous extractant, as indicated above, is preferably substantially free of free halide ions to avoid precipitation of monovalent thallium halides.

The manner in which the carboxylic acid medium containing the dissolved trivalent thallium values, monovalent thallium values and, optionally, alkali metal compound, is contacted with the selected acidic aqueous extractant is not critical to this invention and can be effected employing conventional liquid/liquid extraction techniques and apparatus. Single- or multi-stage extraction techniques can be employed. Thus, the carboxylic acid medium to be treated can be contacted with the acidic aqueous extractant in a batchwise, semi-continuous or continuous manner as by simultaneously introducing the carboxylic acid medium to be treated and the acid aqueous extractant into a stirred vessel and agitating the mixture for intimate blending of the aqueous phase and organic carboxylic acid phase. The resulting mixture can then be passed to a vessel wherein separate aqueous and organic layers are allowed to form. The organic layer comprises the carboxylic acid raffinate rich in trivalent thallium values and can be readily separated. The recovered aqueous phase comprises the extract rich in extracted monovalent thallium and alkali metal values, and can be either recycled for admixture with additional carboxylic acid medium to remove additional trivalent thallium values therefrom, or, when desired, contacted with molecular oxygen or an organic hydroperoxide in the presence of a suitable catalyst (e.g., in accordance with any of the processes of Ser. Nos. 740,147 or 789,053, referred to above) to convert the monovalent thallium values contained therein to the trivalent state.

Alternatively, as is preferred, the carboxylic acid medium to be treated can be contacted with the acidic aqueous extractant by use of conventional countercurrent liquid/liquid extraction techniques. Conventional extraction apparatus can be employed.

The relative amounts of carboxylic acid medium and acidic aqueous extractant which are contacted can be varied widely and is solely a question of economics. Thus, the optimum volume of extractant can be easily ascertained by the skilled practitioner. Generally, however, for carboxylic acid media containing from about 0.01 to 3 moles per liter monovalent thallium values, from about 0.1 to 10 volumes of acidic aqueous extractant are employed per unit volume carboxylic acid medium to be treated to effect extraction of at least about 20 weight percent, preferably at least about 70 weight percent, of the monovalent thallium values.

Likewise, the carboxylic acid medium and acidic aqueous extractant can be contacted under a wide variety of temperature and pressure conditions. Thus, the temperature employed can range from 5° C. to the bubble point of the carboxylic acid medium treated or the acidic aqueous extractant, whichever is lower boiling, and preferably from 20° to 80° C. Pressure is not a parameter of the process of this invention, and a pressure sufficient to maintain at least part of the carboxylic acid medium to be treated and at least part of the acidic aqueous extractant in the liquid form will be suitable. Generally, the pressure will be from about 0.5 to 10 atm., preferably from about 1 to 2 atm.

The acidic aqueous extract can contain the extracted monovalent thallium values, together with alkali metal values, in a wide variety of concentrations and typically will contain from about 0.01 to 3 moles per liter, preferably from about 0.1 to 2 moles per liter, monovalent thallium values; and (when present in the carboxylic acid medium which is treated) from about 0.01 to 3 moles per liter, preferably from about 0.1 to 2 moles per liter, alkali metal values. The acidic aqueous extract can also contain up to about 2 moles per liter trivalent thallium values, and preferably less than 0.5 mole per liter trivalent thallium values. However, higher or lower amounts of the foregoing components can be present. The acidic aqueous extract can also contain up to about 20 weight percent, preferably up to only about 1 weight percent, carboxylic acid due to the limited solubility of carboxylic acid in the acidic aqueous medium.

The carboxylic acid raffinate containing trivalent thallium values and depleted of monovalent thallium and alkali metal values can be withdrawn as product, and, where the trivalent thallium values are, for example, in the form of a carboxylate, can be used (either directly or after evaporation of a portion of the carboxylic acid content of the raffinate to concentrate the liquid with respect to the trivalent thallium) as source of trivalent thallium carboxylate for epoxidizing olefins in accordance with U.S. Pat. No. 3,641,067.

The invention will be more fully understood by reference to the following specific examples, but it is to be understood that these examples are given solely for illustrative purposes and are not intended to be limitative of the invention. In the examples, the determination of trivalent thallium values is by complexometric titration with ethylene diamine tetraacetic acid, which method is sensitive to a concentration of 0.005 mole per liter, and the determination of monovalent thallium values is by potassium permangate titration. Alkali metal values are determined by a non-aqueous titration using perchloric acid in acetic acid; acetic anhydride is added to the sample before titration in an amount sufficient to eliminate any water present. In the examples that follow and throughout the specification, concentrations are expressed in terms of moles per liter unless otherwise indicated. In the examples, the acidic aqueous solutions employed as extractants possess a pH of less than 6. The Tables of data in the following Examples report concentrations of monovalent thallium, trivalent thallium alkali metal values as the respective cations.

The invention will be more fully understood by reference to the following specific examples, but it is to be understood that these examples are given solely for illustrative purposes and are not intended to be limiting of the invention.

EXAMPLE 1

In a series of extractions, a carboxylic acid medium containing octanoic acid and dissolved thallic acetate, thallous acetate and potassium acetate is extracted with the selected quantity of an extractant comprising an acidic aqueous solution containing 3 weight percent acetic acid, by passing the octanoic acid medium and the extractant to a 150 cc separatory funnel and agitating the funnel contents to intimately admix the separate phases. The agitation is continued for about five minutes, whereupon the mixture is allowed to stand and separate phases allowed to form. The aqueous extract and the octanoic acid raffinate are recovered and analyzed.

In the initial extraction, the carboxylic acid medium comprises an octanoic acid solution containing 0.23 mole per liter thallic acetate, 0.11 mole per liter thallous acetate, and 0.45 mole per liter potassium acetate. In each subsequent extraction, the carboxylic acid medium to be extracted comprises the octanoic acid raffinate obtained from the preceding extraction.

The data thereby obtained are set forth in Table 1 below, and indicate (1) that after two extractions, 45 mole percent of the thallous values and 60 mole percent of the potassium values originally present in the carboxylic acid medium are removed and (2) that after 4 extractions, 59 mole percent of the thallous values and 73 mole percent of the potassium values originally present in the initial carboxylic acid medium is removed and 91 mole percent of the thallic acetate originally present in the initial carboxylic acid medium remains in the final carboxylic raffinate. (In Table 1 and in the Tables that follow, "R" is defined as the number of unit volumes of acidic aqueous extractant employed per unit volume of treated carboxylic acid medium.)

TABLE 1

| ract No. | R' | Octanoic Acid Raffinate | | | Aqueous Extract | | | Equilibrium Coefficient | | |
|---|---|---|---|---|---|---|---|---|---|---|
| | | $Tl^{+3}$ | $Tl^{+1}$ | $K^+$ | $Tl^{+3}$ | $Tl^{+1}$ | $Kl^+$ | $k'_{Tl3}$ | $k'_{Tl1}$ | $k'K$ |
| 1 | 1.0 | .22 | .08 | .21 | .01 | .04 | .21 | 22.0 | 2.0 | 1.0 |
| 2 | 1.0 | .22 | .06 | .18 | .01 | .02 | .07 | 22.0 | 3.0 | 2.6 |
| 3 | 1.0 | .21 | .05 | .15 | .01 | .01 | .05 | 21.0 | 5.0 | 3.0 |
| 4 | 1.0 | .21 | .045 | .12 | .01 | .01 | .04 | 21.0 | 4.5 | 3.0 |

EXAMPLE 2-FOR COMPARISON

The procedure of Example 1 is repeated except that the extractant comprises water and the carboxylic acid medium contacted in the initial extraction comprises an octanoic acid solution containing 0.21 mole per liter thallic acetate, 0.12 mole per liter thallous acetate, and 0.4 mole per liter potassium acetate.

The data thereby obtained are set forth in Table 2 below, and indicate that after 2 extractions, only 33 mole percent of the thallous values and 40 mole percent of the potassium values originally present in the initial carboxylic acid medium is removed. Thus, the process of the present invention illustrated in Example 1 allows removal of 73% and 67% more thallous and potassium values, respectively, than when water alone is used as extractant.

TABLE 2

| Extrac. No. | R' | Octanoic Acid Raffinate | | | Aqueous Extract | | | Equilibrium Coefficient | | |
|---|---|---|---|---|---|---|---|---|---|---|
| | | $Tl^{+3}$ | $Tl^{+1}$ | $K^+$ | $Tl^{+3}$ | $Tl^{+1}$ | $K^+$ | $k'_{Tl_3}$ | $k_{Tl_1}$ | $k'K$ |
| 1 | 1 | .21 | .09 | .25 | .01 | .04 | .16 | 21 | 2.2 | 1.6 |
| 2 | 1 | .20 | .08 | .24 | .01 | .01 | .02 | 20 | 8.0 | 12.0 |

EXAMPLE 3

The procedure of Example 1 is repeated except that the extractant comprises an acidic aqueous solution containing 6 weight percent of acetic acid, and the carboxylic acid medium contacted in the initial extraction comprises an octanoic acid solution containing 0.21 mole per liter thallic acetate, 0.038 mole per liter thallous acetate, and 0.07 mole per liter potassium acetate.

The data thereby obtained are set forth in Table 3 below, and indicate that after 4 extractions, 58 mole percent of the thallous values and 76 mole percent of the potassium values originally present in the initial carboxylic acid medium is removed and 76 mole percent of the thallic values originally present in the initial carboxylic acid medium remains in the final carboxylic acid raffinate.

TABLE 3

| Extrac. No. | R' | Octanoic Acid Raffinate | | | Aqueous Extract | | | Equilibrium Coefficient | | |
|---|---|---|---|---|---|---|---|---|---|---|
| | | $Tl^{+3}$ | $Tl^{+1}$ | $K^{+1}$ | $Tl^{+3}$ | $Tl^{+1}$ | $K^{+1}$ | $k'_{Tl_3}$ | $k'_{Tl_1}$ | $k'K$ |
| 1 | 1.0 | .20 | .03 | .05 | .01 | .01 | .03 | 20.0 | 3.0 | 1.7 |
| 2 | 1.0 | .18 | .023 | .037 | .01 | .007 | .026 | 18.0 | 3.3 | 1.4 |
| 3 | 1.0 | .17 | .017 | .023 | .01 | .006 | .019 | 17.0 | 2.8 | 1.2 |
| 4 | 1.0 | .16 | .016 | .017 | .01 | .006 | .017 | 16.0 | 2.7 | 1.0 |

EXAMPLE 4

The procedure of Example 3 is repeated except that the carboxylic acid medium contacted in the initial extraction comprises an octanoic acid solution containing 0.22 mole per liter thallic acetate, 0.17 mole per liter thallous acetate, and no alkali metal compound.

The data thereby obtained are set forth in Table 4 below, and indicate that after 3 extractions, 47 mole percent of the thallous values originally present in the initial carboxylic acid medium is removed and 86 mole percent of the thallic values originally present in the initial carboxylic acid medium remains in the final carboxylic acid raffinate.

TABLE 4

| Extra. No. | R' | Octanoic Acid Raffinate | | Aqueous Extract | | Equilibrium Coefficient | |
|---|---|---|---|---|---|---|---|
| | | $Tl^{+3}$ | $Tl^{+1}$ | $Tl^{+3}$ | $Tl^{+1}$ | $k'_{Tl_3}$ | $k'_{Tl_1}$ |
| 1 | 1.0 | .21 | .13 | .01 | .03 | 21.0 | 4.3 |
| 2 | 1.0 | .20 | .11 | .01 | .03 | 20.0 | 4.1 |
| 3 | 1.0 | .19 | .09 | .01 | .02 | 19.0 | 4.5 |

EXAMPLE 5

The procedure of Example 1 is repeated except that the extractant comprises an acidic aqueous solution containing 12 weight percent of acetic acid, and the carboxylic acid medium contacted in the initial extraction comprises an octanoic acid solution containing 0.21 mole per liter thallic acetate, 0.14 mole per liter thallous acetate, and 0.38 mole per liter potassium acetate.

The data thereby obtained are set forth in Table 5 below, and indicate that after 4 extractions, 79 mole percent of the thallous values and 82 mole mole percent of the potassium values originally present in the initial carboxylic acid medium is removed and 71 mole percent of the thallic values originally present in the initial carboxylic acid medium remains in the final carboxylic acid raffinate.

TABLE 5

| Extrac. No. | R' | Octanoic Acid Raffinate | | | Aqueous Extract | | | Equilibrium Coefficient | | |
|---|---|---|---|---|---|---|---|---|---|---|
| | | $Tl^{+3}$ | $Tl^{+1}$ | $K^{+1}$ | $Tl^{+3}$ | $Tl^{+1}$ | $K^{+1}$ | $k'_{Tl_3}$ | $k'_{Tl_1}$ | $k'K$ |
| 1 | 1.0 | .20 | .07 | .2 | .02 | .06 | .22 | 10.0 | 1.2 | 0.9 |
| 2 | 1.0 | .19 | .06 | .15 | .01 | .02 | .07 | 19.0 | 3.0 | 2.1 |
| 3 | 1.0 | .17 | .04 | .1 | .02 | .02 | .06 | 8.5 | 2.0 | 1.7 |
| 4 | 1.0 | .15 | .03 | .07 | .03 | .02 | .05 | 5.0 | 1.5 | 3.6 |

EXAMPLE 6

The procedure of Example 3 is repeated except that the carboxylic acid medium contacted in the initial extraction comprises an octanoic acid solution containing 0.23 mole per liter thallic acetate, 0.14 mole per liter thallous acetate, and 0.18 mole per liter sodium acetate.

The data thereby obtained are set forth in Table 6 below, and indicate that after 2 extractions, 29 mole percent of the thallous acetate and 72 mole percent of the sodium acetate originally present in the intial carboxylic acid medium is removed and 87 mole percent of the thallic acetate originally present in the initial carboxylic acid medium remains in the final carboxylic acid raffinate.

cent of the thallic acetate originally present in the initial carboxylic acid medium remains in the final carboxylic acid raffinate.

TABLE 8

| Extrac. No. | R' | Octanoic Acid Raffinate | | | Aqueous Extract | | | Equilibrium Coefficient | | |
|---|---|---|---|---|---|---|---|---|---|---|
| | | $Tl^{+3}$ | $Tl^{+1}$ | $Rb^{+1}$ | $Tl^{+3}$ | $Tl^{+1}$ | $Rb^{+1}$ | $k'_{Tl3}$ | $k'_{Tl1}$ | $k'_{Rb}$ |
| 1 | 1.0 | .19 | .06 | 0.3 | .006 | .06 | .26 | 31.6 | 1.0 | 1.2 |
| 2 | 1.0 | .2 | .04 | 0.2 | .005 | .02 | .15 | 40 | 2.0 | 1.3 |

EXAMPLE 9

The procedure of Example 1 is repeated except that the extractant comprises an acidic aqueous solution containing 4.8 weight percent of formic acid, and the carboxylic acid medium contacted in the initial extraction comprises an octanoic acid solution containing 0.21 mole per liter thallic acetate, 0.14 mole per liter thallous acetate, and 0.38 mole per liter potassium acetate.

TABLE 6

| Extrac. No. | R' | Octanoic Acid Raffinate | | | Aqueous Extract | | | Equilibrium Coefficient | | |
|---|---|---|---|---|---|---|---|---|---|---|
| | | $Tl^{+3}$ | $Tl^{+1}$ | $Na^{+1}$ | $Tl^{+3}$ | $Tl^{+1}$ | $Na^{+1}$ | $k'_{Tl3}$ | $k'_{Tl1}$ | $K'_{Na}$ |
| 1 | 1.0 | 0.21 | .11 | .07 | .01 | .03 | .11 | 21.0 | 3.7 | 0.6 |
| 2 | 1.0 | 2 | .1 | .05 | .01 | .014 | .036 | 20.0 | 0.7 | 1.4 |

EXAMPLE 7

The procedure of Example 3 is repeated except that the carboxylic acid medium contacted in the initial extraction comprises an octanoic acid solution containing 0.21 mole per liter thallic acetate, 0.11 mole per liter thallous acetate, and 0.37 mole per liter cesium acetate.

The data thereby obtained are set forth in Table 7 below, and indicate that after 3 extractions, 64 mole percent of the thallous acetate and 65 mole percent of the cesium values originally present in the initial carboxylic acid medium is removed and 90 mole percent of the thallic values originally present in the initial carboxylic acid medium remains in the final carboxylic acid raffinate.

The data thereby obtained are set forth in Table 9 below, and indicate that after 3 extractions, 79 mole percent of the thallous values and 87 mole percent of the potassium values originally present in the initial carboxylic acid medium is removed and 90 mole percent of the thallic values originally present in the initial carboxylic acid medium remains in the final carboxylic acid raffinate.

TABLE 9

| Extrac. No. | R' | Octanoic Acid Raffinate | | | Aqueous Extract | | | Equilibrium Coefficient | | |
|---|---|---|---|---|---|---|---|---|---|---|
| | | $Tl^{+3}$ | $Tl^{+1}$ | $K^{+1}$ | $Tl^{+3}$ | $Tl^{+1}$ | $K^{+1}$ | $k'_{Tl3}$ | $k'_{Tl1}$ | $k'K$ |
| 1 | 1.0 | .2 | .06 | .17 | .01 | .07 | .28 | 20.0 | 0.9 | 0.6 |
| 2 | 1.0 | .2 | .04 | .1 | .01 | .03 | .06 | 20.0 | 1.3 | 1.7 |
| 3 | 1.0 | .19 | .03 | .05 | .01 | .02 | .04 | 19.0 | 1.5 | 1.2 |

EXAMPLE 10

The procedure of Example 1 is repeated except that

TABLE 7

| Extrac. No. | R' | Octanoic Acid Raffinate | | | Aqueous Extract | | | Equilibrium Coefficient | | |
|---|---|---|---|---|---|---|---|---|---|---|
| | | $Tl^{+3}$ | $Tl^{+1}$ | $C_s^{+1}$ | $Tl^{+3}$ | $Tl^{+1}$ | $C_s^{+1}$ | $k'_{Tl3}$ | $k'_{Tl1}$ | $k'_{cs}$ |
| 1 | 1.0 | .21 | .06 | .19 | .01 | .04 | .17 | 21.0 | 1.5 | 1.1 |
| 2 | 1.0 | .20 | .05 | .16 | .01 | .02 | .04 | 20.0 | 2.5 | 4.0 |
| 3 | 1.0 | .19 | .04 | .13 | .01 | .01 | .03 | 19 | 4.0 | 4.3 |

EXAMPLE 8

The procedure of Example 3 is repeated except that the carboxylic acid medium contacted in the initial extraction comprises an octanoic acid solution containing 0.2 mole per liter thallic acetate, 0.11 mole per liter thallous acetate, and 0.52 mole per liter rubidium acetate.

The data thereby obtained are set forth in Table 8 below, and indicate that after 2 extractions, 64 mole percent of the thallous acetate and 62 mole percent of the rubidium acetate originally present in the initial carboxylic acid medium is removed and 100 mole perthe extractant comprises an acidic aqueous solution containing 7.4 weight percent of propionic acid, and the carboxylic acid medium contacted in the initial extraction comprises an octanoic acid solution containing 0.23 mole per liter thallic acetate, 0.14 mole per liter thallous acetate, and 0.52 mole per liter potassium acetate.

The data thereby obtained are set forth in Table 10 below, and indicate that after one extraction, 64 mole percent of the thallous values and 56 mole percent of the potassium values originally present in the initial carboxylic acid medium is removed and 96 mole percent of the thallic values originally present in the initial carboxylic acid medium remains in the carboxylic acid raffinate.

TABLE 10

| | Octanoic Acid Raffinate | | | Aqueous Extract | | | Equilibrium Coefficient | | |
|---|---|---|---|---|---|---|---|---|---|
| R' | $Tl^{+3}$ | $Tl^{+1}$ | $K^{+1}$ | $Tl^{+3}$ | $Tl^{+1}$ | $K^{+1}$ | $k'_{Tl3}$ | $k'_{Tl1}$ | $k'K$ |
| 1.0 | .22 | .05 | .23 | .01 | .09 | .29 | 22.0 | 0.6 | 0.8 |

EXAMPLE 11

The procedure of Example 1 is repeated except that the extractant comprises an acidic aqueous solution containing 8.5 weight percent of paratoluene sulfonic acid, and the carboxylic acid medium contacted in the initial extraction comprises an octanoic acid solution containing 0.22 mole per liter thallic acetate, 0.12 mole per liter thallous acetate, and 0.44 mole per liter potassium acetate.

The data thereby obtained are set forth in Table 11 below, and indicate that after 2 extractions, 96 mole percent of the thallous values and 99 mole percent of the potassium values originally present in the initial carboxylic acid medium is removed and 95 mole percent of the thallic values originally present in the initial carboxylic acid medium remains in the final carboxylic acid raffinate.

TABLE 11

| Extrac. No. | R' | Octanoic Acid Raffinate | | | Aqueous Extract | | | Equilibrium Coefficient | | |
|---|---|---|---|---|---|---|---|---|---|---|
| | | $Tl^{+3}$ | $Tl^{+1}$ | $K^{+1}$ | $Tl^{+3}$ | $Tl^{+1}$ | $K^{+1}$ | $k'_{Tl3}$ | $k'_{Tl1}$ | $k'K$ |
| 1 | 1.0 | .22 | .03 | .06 | .004 | .09 | .49 | 55 | 0.3 | .12 |
| 2 | 1.0 | .21 | .005 | .006 | .01 | .02 | .056 | 21 | 0.25 | .11 |

EXAMPLE 12

The procedure of Example 1 is repeated except that the extractant comprises an acidic aqueous solution containing 6 weight percent of acetic acid, and the carboxylic acid medium contacted in the initial extraction comprises a hexanoic acid solution containing 0.2 mole per liter thallic acetate, 0.14 mole per liter thallous acetate, and 0.49 mole per liter potassium acetate.

The data thereby obtained are set forth in Table 12 below, and indicate that after 4 extractions, 70 mole percent of the thallous values and 78 mole percent of the potassium values originally present in the initial carboxylic acid medium is removed and about 100 mole percent of the thallic values originally present in the initial carboxylic acid medium remains in the final carboxylic acid raffinate.

TABLE 12

| Extrac. No. | R' | Hexanoic Acid Raffinate | | | Aqueous Extract | | | Equilibrium Coefficient | | |
|---|---|---|---|---|---|---|---|---|---|---|
| | | $Tl^{+3}$ | $Tl^{+1}$ | $K^{+1}$ | $Tl^{+3}$ | $Tl^{+1}$ | $K^{+1}$ | $k'_{Tl3}$ | $k'_{Tl1}$ | $k'K$ |
| 1 | 1.0 | .21 | .09 | .27 | .01 | .05 | .24 | 21 | 1.8 | 1.1 |
| 2 | 1.0 | .21 | .06 | .19 | .01 | .03 | .1 | 21 | 2.0 | 1.9 |
| 3 | 1.0 | .20 | .05 | .15 | .01 | 0.14 | .07 | 20 | 3.6 | 2.3 |
| 4 | 1.0 | .21 | .042 | .11 | .01 | .014 | .05 | 21 | 3.0 | 2.1 |

EXAMPLE 13 FOR COMPARISON

The procedure of Example 12 is repeated except that the extractant comprises water. The data thereby obtained are set forth in Table 13 below, and indicate that after 4 extractions only 50 mole percent of the thallous values and 69 mole percent of the potassium values originally present in the initial carboxylic acid medium is removed.

TABLE 13

| Extrac. No. | R' | Hexanoic Acid Raffinate | | | Aqueous Extract | | | Equilibrium Coefficient | | |
|---|---|---|---|---|---|---|---|---|---|---|
| | | $Tl^{+3}$ | $Tl^{+1}$ | $K^{+1}$ | $Tl^{+3}$ | $Tl^{+1}$ | $K^{+1}$ | $k'_{Tl3}$ | $k'_{Tl1}$ | $k'K$ |
| 1 | 1.0 | .19 | .1 | .3 | .01 | .04 | .23 | 19 | 2.5 | 1.3 |
| 2 | 1.0 | .19 | .08 | .23 | .004 | .02 | .11 | 47.5 | 4.0 | 2.1 |
| 3 | 1.0 | .19 | .07 | .18 | .004 | .01 | .06 | 47.5 | 7.0 | 3.0 |
| 4 | 1.0 | .18 | .07 | .15 | .02 | .01 | .04 | 9.0 | 7.0 | 3.5 |

EXAMPLE 14

The procedure of Example 1 is repeated except that the extractant comprises an acidic aqueous solution containing 6 weight percent of acetic acid, and the carboxylic acid medium contacted in the initial extraction comprises a neo-decanoic acid solution containing 0.23 mole per liter thallic acetate, 0.07 mole per liter thallous acetate, and 0.19 mole per liter potassium acetate.

The data thereby obtained are set forth in Table 14 below, and indicate that after 4 extractions, 80 mole percent of the thallous values and 84 mole percent of the potassium values originally present in the initial carboxylic acid medium is removed and 74 mole percent of the thallic values originally present in the initial carboxylic acid medium remains in the final carboxylic acid raffinate.

TABLE 14

| Extrac. No. | R' | Neodecanoic Acid Raffinate | | | Aqueous Extract | | | Equilibrium Coefficient | | |
|---|---|---|---|---|---|---|---|---|---|---|
| | | $Tl^{+3}$ | $Tl^{+1}$ | $K^{+1}$ | $Tl^{+3}$ | $Tl^{+1}$ | $K^{+1}$ | $k'_{Tl_3}$ | $k'_{Tl_1}$ | $k'K$ |
| 1 | 1.0 | .22 | .05 | .1 | .01 | .02 | .1 | 22 | 2.5 | 1.0 |
| 2 | 1.0 | .20 | .035 | .065 | .01 | .014 | .05 | 20 | 2.5 | 1.3 |
| 3 | 1.0 | .19 | .026 | .049 | .01 | .01 | .02 | 19 | 2.6 | 2.5 |
| 4 | 1.0 | .17 | .014 | .03 | .01 | .007 | .008 | 17 | 2.0 | 3.9 | carboxylic acid medium remains in the final carboxylic acid raffinate.

TABLE 16

| Extrac. No. | R' | 2-Ethylhexanoic Acid Raffinate | | | Aqueous Extract | | | Equilibrium Coefficient | | |
|---|---|---|---|---|---|---|---|---|---|---|
| | | $Tl^{+3}$ | $Tl^{+1}$ | $K^{+1}$ | $Tl^{+3}$ | $Tl^{+1}$ | $K^{+1}$ | $k'_{Tl_3}$ | $k'_{Tl_1}$ | $k'K$ |
| 1 | 1.0 | .22 | .057 | .18 | .01 | .026 | .1 | 22 | 2.2 | 1.8 |
| 2 | 1.0 | .22 | .05 | .15 | .01 | .01 | .085 | 22 | 5.0 | 2.3 |
| 3 | 1.0 | .21 | .04 | .11 | .01 | .01 | .05 | 21 | 4.2 | 2.2 |
| 4 | 1.0 | .21 | .04 | .08 | .01 | .005 | .04 | 21 | 8.0 | 2.9 |

EXAMPLE 15 FOR COMPARISON

The procedure of Example 14 is repeated except that the extractant comprises water and the carboxylic acid medium contacted in the initial extraction comprises a neodecanoic acid solution containing 0.23 mole per liter thallic acetate, 0.05 mole per liter thallous acetate, and 0.21 mole per liter potassium acetate.

The data thereby obtained are set forth in Table 15 below, and indicate that after 4 extractions essentially none of the thallous values and only 57 mole percent of the potassium acetate originally present in the initial carboxylic acid medium is removed.

TABLE 15

| Extrac. No. | R' | Neodecanoic Acid Raffinate | | | Aqueous Extract | | | Equilibrium Coefficient | | |
|---|---|---|---|---|---|---|---|---|---|---|
| | | $Tl^{+3}$ | $Tl^{+1}$ | $K^{+1}$ | $Tl^{+3}$ | $Tl^{+1}$ | $K^{+1}$ | $k'_{Tl_3}$ | $k'_{Tl_1}$ | $k'K$ |
| 1 | 1.0 | .23 | .05 | .17 | .01 | .007 | .06 | 23.0 | 7.1 | 2.8 |
| 2 | 1.0 | .22 | .05 | .14 | .01 | .003 | .03 | 22.0 | 16.7 | 4.7 |
| 3 | 1.0 | .21 | .05 | .1 | .01 | .003 | .036 | 21.0 | 16.7 | 2.8 |
| 4 | 1.0 | .21 | .05 | .09 | .01 | .003 | .027 | 21.0 | 16.7 | 3.3 |

EXAMPLE 17 FOR COMPARISON

The procedure of Example 16 is repeated except that the extractant comprises water and the carboxylic acid medium contacted in the initial extraction comprises a 2-ethyl hexanoic acid solution containing 0.24 mole per liter thallic acetate, 0.08 mole per liter thallous acetate, and 0.33 mole per liter potassium acetate.

The data thereby obtained are set forth in Table 17 below, and indicate that after 4 extractions, only 35 mole percent of the thallous values and 48 mole percent of the potassium values originally present in the initial carboxylic acid medium is removed.

TABLE 17

| Extrac. No. | R' | 2-Ethylhexanoic Acid Raffinate | | | Aqueous Extract | | | Equilibrium Coefficient | | |
|---|---|---|---|---|---|---|---|---|---|---|
| | | $Tl^{+3}$ | $Tl^{+1}$ | $K^{+1}$ | $Tl^{+3}$ | $Tl^{+1}$ | $K^{+1}$ | $k'_{Tl_3}$ | $k'_{Tl_1}$ | $k'K$ |
| 1 | 1.0 | .24 | .06 | .18 | .002 | .002 | .15 | 120 | 8.0 | 1.2 |
| 2 | 1.0 | .24 | .056 | .18 | .001 | .006 | .047 | 240 | 9.3 | 3.8 |
| 3 | 1.0 | .24 | .052 | .17 | .001 | .002 | .03 | 240 | 26.0 | 5.7 |
| 4 | 1.0 | .24 | .052 | .17 | .001 | .002 | .025 | 240 | 26.0 | 6.8 |

EXAMPLE 16

The procedure of Example 1 is repeated except that the extractant comprises an acidic aqueous solution containing 6 weight percent of acetic acid, and the carboxylic acid medium contacted in the initial extraction comprises a 2-ethyl hexanoic acid solution containing 0.23 mole per liter thallic acetate, 0.08 mole per liter thallous acetate, and 0.24 mole per liter potassium acetate.

The data thereby obtained are set forth in Table 16 below, and indicate that after 4 extractions, 50 mole percent of the thallous values and 67 mole percent of the potassium values originally present in the initial carboxylic acid medium is removed and 91 mole percent of the thallic values originally present in the initial

EXAMPLE 18

The procedure of Example 1 is repeated in six series of extractions using different acidic aqueous extractants. In each run the carboxylic acid medium contacted in the initial extraction comprises an octanoic acid solution containing 0.24 mole per liter thallic acetate, 0.12 mole per liter thallous acetate, and 0.41 mole per liter potassium acetate. The acidic aqueous extractants contain the acidifying agents indicated in Table 18.

The data obtained, which are set forth in Table 18 below, indicate that at the end of each series of extractions the amounts of thallous values and potassium values removed from the carboxylic acid medium and the amounts of thallic values remaining in the final octanoic acid raffinate (relative to the initial concentrations of these components in the initial carboxylic acid medium) are as follows:

| Series | $Tl^{+1}$ Removed (Mole %) | $K^{+1}$ Removed (Mole %) | $Tl^{+3}$ Remaining (Mole %) |
|---|---|---|---|
| A | 97 | 99.8 | 88 |
| B | 98 | 98 | approx. 100 |
| C | 67 | 66 | " 100 |
| D | 50 | 68 | " 100 |
| E | 92 | 95 | 87 |
| F | 92 | 93 | 83 | plished to an efficiency of about 71.3 percent based on the thallic values charged.

EXAMPLE 20

Following the procedure of Example 1, a carboxylic acid medium comprising an octanoic acid solution containing 0.24 mole per liter thallic acetate, 0.23 mole per liter thallous acetate, and 1.0 mole per liter potassium acetate, is subjected to five extractions with fresh portions of an acidic aqueous solution containing 1.0 M isobutyric acid.

The data thereby obtained are set forth in Table 19 below, and indicate that after 5 extractions, 83 mole percent of the thallous values and 90 mole percent of the potassium values originally present in the initial

TABLE 18

| Series | Extrac. No. | Aqueous Extractant Composition | R' | Octanoic Acid Raffinate | | | Aqeuous Extract | | | Equilibrium Coefficient | | |
|---|---|---|---|---|---|---|---|---|---|---|---|---|
| | | | | $Tl^{+3}$ | $Tlhu_{+1}$ | $K^{+1}$ | $Tl^{+3}$ | $Tl^{+1}$ | $K^{+1}$ | $k'_{Tl3}$ | $k'_{Tl1}$ | $k'K$ |
| A | 1 | 1.0 N $H_2SO_4$ | 1.0 | .22 | .007 | .03 | .01 | .1 | .30 | 22.0 | 0.07 | 0.08 |
| | 2 | " | 1.0 | .21 | .004 | .001 | .01 | .005 | .02 | 21.0 | 0.8 | 0.02 |
| B | 1 | 0.5 N $HNO_3$ | 1.0 | .23 | .02 | .1 | .01 | .1 | .32 | 23.0 | 0.2 | 0.3 |
| | 2 | " | 1.0 | .23 | .002 | .008 | .01 | .02 | .09 | 23.0 | 0.1 | 0.09 |
| C | 1 | 1.0 N $H_3PO_4$ | 1.0 | .24 | .07 | .2 | .004 | .06 | .21 | 60.0 | 1.2 | 1.0 |
| | 2 | " | 1.0 | .23 | .04 | .1 | .004 | .03 | .1 | 58.5 | 1.3 | 1.0 |
| D | 1 | Saturated aqueous phenol | 1.0 | .23 | 0.08 | .18 | .003 | .04 | .18 | 76.7 | 2.0 | 1.0 |
| | 2 | " | 1.0 | .23 | 0.06 | .13 | .01 | .02 | .06 | 23.0 | 3.0 | 2.2 |
| E | 1 | 1.0 M $ClCH_2COOH$ | 1.0 | .23 | .05 | .17 | .01 | .06 | .26 | 23.0 | 0.8 | 0.65 |
| | 2 | " | 1.0 | .22 | .03 | .09 | .01 | .03 | .08 | 22.0 | 1.0 | 1.1 |
| | 3 | " | 1.0 | .22 | .02 | .04 | .01 | .01 | .07 | 22.0 | 2.0 | 0.6 |
| | 4 | " | 1.0 | .2 | .01 | .02 | .02 | .01 | .03 | 10.0 | 1.0 | 0.7 |
| F | 1 | 1.0 M $Cl_2CHCOOH$ | 1.0 | .22 | .05 | .15 | .01 | .07 | .3 | 22.0 | 0.7 | 0.5 |
| | 2 | " | 1.0 | .21 | .02 | .06 | .01 | .03 | .13 | 21.0 | 0.7 | 0.5 |
| | 3 | " | 1.0 | .19 | .01 | .03 | .01 | .01 | .08 | 19.0 | 1.0 | 0.4 |

EXAMPLE 19

An octanoic acid liquid containing dissolved therein 0.09 mmol/cc thallic acetate, 0.03 mmol/cc thallous acetate and 0.1 mmol/cc potassium acetate are passed as feed at a rate of about 451 parts per hour to the lower portion of an eleven-stage continuous countercurrent Schiebel extractor. To the upper portion of the extracted there is passed, at a rate of 1493 parts per hour, an extractant comprising an aqueous acetic acid solution cpmtaoming about 4.5 weight percent acetic acid. An aqueous extract is withdrawn from the lower portion of the extractor at a rate of about 1600 parts per hour, and is found to contain 0.008 mmol/cc thallous values, 0.004 mmol/cc thallic values and 0.05 mmol/cc potassium values. From the upper portion of the extractor there is drawn at a rate of 460 parts per hour an octanoic acid depleted of thallous values and potassium values and containing 0.008 mmol/cc thallous values, 0.004 mmol/cc potassium values and 0.065 mmol/cc thallic values. Thus, recovery of thallic values is accomcarboxylic acid medium is removed and 92 mole percent of the thallic values originally present in the initial carboxylic acid medium remains in the final carboxylic acid raffinate.

TABLE 19

| Extrac. No. | R' | Isobutyric Acid Raffinate | | | Aqueous Extract | | | Equilibrium Coefficient | | |
|---|---|---|---|---|---|---|---|---|---|---|
| | | $Tl^{+3}$ | $Tl^{+1}$ | $K^{+1}$ | $Tl^{+3}$ | $Tl^{+1}$ | $K^{+1}$ | $k'_{Tl3}$ | $k'_{Tl1}$ | $k'_K$ |
| 1 | 1.0 | .23 | .12 | .42 | .01 | .11 | .62 | 23 | 1.1 | 0.7 |
| 2 | 1.0 | .23 | 0.75 | .24 | .01 | .042 | .19 | 23 | 1.8 | 1.3 |
| 3 | 1.0 | .23 | .06 | .18 | .01 | .02 | .06 | 23 | 3.0 | 3.0 |
| 4 | 1.0 | .23 | .05 | .14 | .01 | .01 | .04 | 23 | 5.0 | 3.5 |
| 5 | 1.0 | .23 | .04 | .1 | .01 | .007 | .04 | 23 | 5.7 | 2.5 |

EXAMPLE 21

To a liquid comprising benzene 1.0 M in octanoic acid is added sufficient thallic acetate, thallous acetate, and potassium acetate to provide concentrations of these salts of 0.23, 0.08, and 0.2 mole per liter, respectively. Following the procedure of Example 1, the carboxylic acid medium so produced is extracted with fresh portions of an extractant comprising an aqueous solution containing 6 weight percent acetic acid.

The data thereby obtained are set forth in Table 19 below, and indicate that after 2 extractions, 50 mole percent of thallous values and 90 mole percent of the potassium values originally present in the initial carboxylic acid medium is removed and 61 mole percent of the thallic values originally present in the initial carboxylic acid raffinate.

TABLE 20

| Extrac. Run | R' | Octanoic Acid Raffinate | | | Aqueous Extract | | | Equilibrium Coefficient | | |
|---|---|---|---|---|---|---|---|---|---|---|
| | | $Tl^{+3}$ | $Tl^{+1}$ | $K^{+1}$ | $Tl^{+3}$ | $Tl^{+1}$ | $K^{+1}$ | $k'_{Tl3}$ | $k'_{Tl1}$ | $k'K$ |
| 1 | 1.0 | .18 | .05 | .08 | .05 | .03 | .13 | 3.6 | 1.7 | 0.6 |
| 2 | 1.0 | .14 | .04 | .02 | .04 | .02 | .06 | 3.5 | 1.5 | 0.3 |

EXAMPLE 22

To a liquid comprising benzene 3.0 M in octanoic acid is added to sufficient thallic acetate, thallous acetate, and potassium acetate to provide concentrations of these salts of 0.2, 0.07, and 0.18 mole per liter, respectively. Following the procedure of Example 1, the carboxylic acid medium so produced is extracted with fresh portions of extractant comprising an aqueous solution containing 3 weight percent acetic acid.

The data thereby obtained are set forth in Table 21 below, and indicate that after 2 extractions, 43 mole percent of the thallous values and 78 mole percent of the potassium values originally present in the initial carboxylic acid medium is removed and 75 mole percent of the thallic values originally present in the initial carboxylic acid medium remains in the final carboxylic acid raffinate.

TABLE 21

| Extrac. Run | R' | Octanoic Acid Raffinate | | | Aqueous Extract | | | Equilibrium Coefficient | | |
|---|---|---|---|---|---|---|---|---|---|---|
| | | $Tl^{+3}$ | $Tl^{+1}$ | $K^{+1}$ | $Tl^{+3}$ | $Tl^{+1}$ | $K^{+1}$ | $k'_{Tl3}$ | $k'_{Tl1}$ | $k'K$ |
| 1 | 1.0 | .17 | .05 | .09 | .03 | .02 | .1 | 5.7 | 2.5 | 0.9 |
| 2 | 1.0 | .15 | .04 | .04 | .02 | .01 | .03 | 7.5 | 4.0 | 1.3 |

EXAMPLE 23 FOR COMPARISON

The procedure of Example 22 is repeated except that the extractant comprises water.

The data thereby obtained are set forth in Table 22 below, and indicate that after 2 extractions, only 20 mole percent of the thallous values and only 56 mole percent of the potassium values originally present in the initial carboxylic acid medium is removed.

TABLE 22

| Extrac. Run | R' | Octanoic Acid Raffinate | | | Aqueous Extract | | | Equilibrium Coefficient | | |
|---|---|---|---|---|---|---|---|---|---|---|
| | | $Tl^{+3}$ | $Tl^{+1}$ | $K^{+1}$ | $Tl^{+3}$ | $Tl^{+1}$ | $K^{+1}$ | $k'_{Tl3}$ | $k'_{Tl1}$ | $k'K$ |
| 1 | 1.0 | .19 | .06 | .1 | .01 | .01 | .09 | 19.0 | 6.0 | 1.1 |
| 2 | 1.0 | .19 | .056 | .08 | .01 | .003 | .027 | 19.0 | 18.6 | 1.0 |

EXAMPLE 24

To a liquid comprising methyl caproate 3.5 M in octanoic acid is added to sufficient thallic acetate, thallous acetate, and potassium acetate to provide concentrations of these salts of 0.22, 0.06, and 0.2 mole per liter, respectively. Following the procedure of Example 1, the carboxylic acid medium so produced is extracted with fresh portions of extractant comprising an aqueous solution containing 6.0 weight percent acetic acid.

The data thereby obtained are set forth in Table 23 below, and indicate that after 2 extractions, 67 mole percent of the thallous values and 80 mole percent of the potassium values originally present in the initial carboxylic acid medium is removed and 55 mole percent of the thallic values originally present in the initial carboxylic acid medium remains in the final carboxylic acid raffinate.

TABLE 23

| Extrac. Run | R' | Octanoic Acid Raffinate | | | Aqueous Extract | | | Equilibrium Coefficient | | |
|---|---|---|---|---|---|---|---|---|---|---|
| | | $Tl^{+3}$ | $Tl^{+1}$ | $K^{+1}$ | $Tl^{+3}$ | $Tl^{+1}$ | $K^{+1}$ | $k'_{Tl3}$ | $k'_{Tl1}$ | $k'K$ |
| 1 | 1.0 | .17 | .03 | .1 | .05 | .03 | .11 | 3.4 | 1.0 | 0.9 |
| 2 | 1.0 | .12 | .02 | .04 | .05 | .016 | .064 | 2.4 | 1.2 | 0.6 |

EXAMPLE 25

To a liquid comprising $CH_2Cl_2$ 3.0 M in hexanoic acid is added to sufficient thallic acetate, thallous acetate, and potassium acetate to provide concentrations of these salts of 0.22, 0.1 and 0.17 mole per liter, respectively. Following the procedure of Example 1, the carboxylic acid medium so produced is extracted with fresh portions of extractant comprising an aqueous solution containing 6 weight percent acetic acid.

The data thereby obtained are set forth in Table 24 below, and indicate that after 2 extractions, 60 mole percent of the thallous values and 82 mole percent of the potassium values originally present in the initial carboxylic acid medium is removed and 55 mole percent of the thallic values originally present in the initial carboxylic acid medium remains in the final carboxylic acid raffinate.

TABLE 24

| Extrac. Run | R' | Octanoic Acid Raffinate | | | Aqueous Extract | | | Equilibrium Coefficient | | |
|---|---|---|---|---|---|---|---|---|---|---|
| | | $Tl^{+3}$ | $Tl^{+1}$ | $K^{+1}$ | $Tl^{+3}$ | $Tl^{+1}$ | $K^{+1}$ | $k'_{Tl3}$ | $k'_{Tl1}$ | $k'K$ |
| 1 | 1.0 | .17 | .05 | .08 | .05 | .05 | .07 | 3.4 | 1.0 | 0.9 |
| 2 | 1.0 | .12 | .04 | .03 | .05 | .02 | .05 | 2.4 | 2.0 | 0.6 |

EXAMPLE 26

To a liquid comprising benzene 4.0 M in hexanoic acid is added to sufficient thallic acetate, thallous acetate, and potassium acetate to provide concentrations of these salts of 0.22, 0.09, and 0.23 mole per liter, respectively. Following the procedure of Example 1, the carboxylic acid medium so produced is extracted with fresh portions of extractant comprising an aqueous solution containing 6.0 weight percent acetic acid.

The data thereby obtained are set forth in Table 25 below, and indicate that after 2 extractions, 56 percent of the thallous values and 83 mole percent of the potassium values originally present in the initial carboxylic acid medium is removed and 75 mole percent of the thallic values originally present in the initial carboxylic acid medium remains in the final carboxylic acid raffinate.

TABLE 25

| Extrac. Run | R' | Octanoic Acid Raffinate | | | Aqueous Extract | | | Equilibrium Coefficient | | |
|---|---|---|---|---|---|---|---|---|---|---|
| | | $Tl^{+3}$ | $Tl^{+1}$ | $K^{+1}$ | $Tl^{+3}$ | $Tl^{+1}$ | $K^{+1}$ | $k'_{Tl3}$ | $k'_{Tl1}$ | $k'K$ |
| 1 | 1.0 | .19 | .06 | .11 | .04 | .03 | .13 | 4.8 | 2.0 | 0.8 |
| 2 | 1.0 | .15 | .04 | .04 | .04 | .02 | .06 | 3.8 | 2.8 | 0.7 |

EXAMPLE 27

To a liquid comprising benzene, 4.0 M in hexanoic acid is added to sufficient thallic acetate, thallous acetate, and potassium acetate to provide concentrations of these salts of 0.4, 0.2, and 0.4 mole per liter, respectively. Following the procedure of Example 1, the carboxylic acid medium so produced is extracted with fresh portions of extractant comprising an aqueous solution containing 6 weight percent acetic acid.

The data thereby obtained are set forth in Table 26 below, and indicate that after 2 extractions, 56 mole percent of the thallous values and 70 mole percent of the potassium values originally present in the initial carboxylic acid medium is removed and 70 mole percent of the thallic values originally present in the initial carboxylic acid medium remains in the final carboxylic acid raffinate.

TABLE 26

| Extrac. Run | R' | Octanoic Acid Raffinate | | | Aqueous Extract | | | Equilibrium Coefficient | | |
|---|---|---|---|---|---|---|---|---|---|---|
| | | $Tl^{+3}$ | $Tl^{+1}$ | $K^{+1}$ | $Tl^{+3}$ | $Tl^{+1}$ | $K^{+1}$ | $k'_{Tl3}$ | $k'_{Tl1}$ | $k'K$ |
| 1 | 1.0 | .34 | .11 | .19 | .06 | .08 | .27 | 5.7 | 1.4 | 0.7 |
| 2 | 1.0 | .28 | .09 | .12 | .06 | .03 | .07 | 4.5 | 3.0 | 1.7 |

It will be obvious that various changes and modifications may be made without departing from the invention and it is intended, therefore, that all matter contained in the foregoing description shall be interpreted as illustrative only and not limitative of the invention.

I claim:

1. A process for extractively removing monovalent thallium values from a liquid medium containing a carboxylic acid having limited solubility in water and containing dissolved trivalent thallium values and monovalent thallium values which comprises contacting the carboxylic acid medium with an extractant comprising an acidic aqueous medium to preferentially extract monovalent thallium values into the aqueous medium, and recovering a carboxylic acid raffinate containing trivalent thallium values and depleted in monovalent thallium values.

2. The process according to claim 1 wherein the carboxylic acid comprises at least one member selected from the group consisting of monocarboxylic acids of the formula:

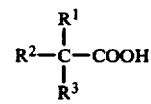

wherein $R^1$, $R^2$, and $R^3$ are the same or different and are selected from the group consisting of hydrogen, alkyl, cycloalkyl, aryl, alkarayl, aralkyl, derivatives of the foregoing groups wherein one or more carbon-bonded hydrogen atom is replaced by an alkyl, cycloalkyl or aryl group or by a halide atom, and derivatives of the foregoing groups wherein one or more carbon atom is replaced by an oxygen atom, with the proviso that $R^3$ cannot be hydrogen when $R^1$ and $R^2$ are each hydrogen, and with the further proviso that the monocarboxylic acid possesses at least 5 carbon atoms per acid molecule.

3. The process of claim 1 wherein the carboxylic acid comprises a monocarboxylic acid having at least six carbon atoms per molecule.

4. The process of claim 1 wherein the carboxylic acid has a solubility in water at 20° C. of less than about 2 grams of acid per 100 grams of water.

5. The process of claim 1 wherein the trivalent thallium values present in the carboxylic acid medium comprises a thallic salt of an alkyl carboxylic acid having at least 6 carbon atoms per acid molecule.

6. The process according to claim 1 wherein the acidic aqueous medium contains an acidifying agent comprising a member selected from the group consisting of phenol, mineral acids, sulfonic acids, lower alkanoic acids, halogenated derivatives of lower alkanoic acids and mixtures thereof.

7. The process according to claim 6 wherein the acidifying agent comprises a member selected from the group consisting of sulfuric acid, nitric acid, phosphoric acid, perchloric acid, formic acid, acetic acid, propionic acid, butyric acid, isobutyric acid, the halo-acetic acids, para-toluene sulfonic acid, methane sulfonic acid, and mixtures thereof.

8. The process according to claim 1 wherein the carboxylic acid medium to be treated also contains dissolved therein at least one alkali metal compound, and wherein at least a portion of said dissolved alkali metal values are extracted into the aqueous medium, thereby producing a carboxylic acid raffinate also depleted of alkali metal values.

* * * * *